United States Patent [19]
Gombatz et al.

[11] Patent Number: 5,659,084
[45] Date of Patent: Aug. 19, 1997

[54] PROCESSES AND INTERMEDIATES FOR THE PREPARATION OF 2-SUBSTITUTED BENZALDEHYDES

[75] Inventors: Kerry Joseph Gombatz, West Chester, Pa.; Michael Anthony Forth; Jerome Francis Hayes, both of Tonbridge, Great Britain; Michael Barry Mitchell, Basking Ridge, N.J.; Stephen Alexander Smith, Tonbridge, Great Britain

[73] Assignees: SmithKline Beecham Corporation, Philadelphia, Pa.; SmithKline Beecham plc, Brentford, England

[21] Appl. No.: 307,730

[22] PCT Filed: Mar. 25, 1993

[86] PCT No.: PCT/US93/02803

§ 371 Date: Dec. 7, 1994

§ 102(e) Date: Dec. 7, 1994

[87] PCT Pub. No.: WO93/19033

PCT Pub. Date: Sep. 30, 1993

[51] Int. Cl.$^6$ .................................................. C07C 209/42
[52] U.S. Cl. .......................... 564/272; 564/409; 564/414; 568/426; 568/436
[58] Field of Search ...................... 564/272, 409, 564/414; 568/426, 436

[56] References Cited

U.S. PATENT DOCUMENTS

| | | |
|---|---|---|
| 3,466,164 | 9/1969 | De Gaetano et al. |
| 3,637,851 | 1/1972 | Rumanowski. |
| 3,910,944 | 10/1975 | Gall. |
| 4,198,349 | 4/1980 | Nuss, Jr. et al. |
| 4,231,962 | 11/1980 | Reinehr et al. |
| 4,820,719 | 4/1989 | Gleason et al. |

FOREIGN PATENT DOCUMENTS

| | | |
|---|---|---|
| 0217269 | 4/1987 | European Pat. Off. |

OTHER PUBLICATIONS

*J. Org. Chem*, vol. 49, No. 6, Watanabe et al. (1984) pp. 742–749.

*Advanced Organic Chem.*, 1977, Second Ed., Mar., J. pp. 805–807.

*J. Org. Chem*, vol. 41, No. 9, Ziegler et al. (1965) pp. 1564–1566.

*J. Org. Chem*, vol. 43, No. 21, Murahashi et al. (1978) pp. 4099–4106.

*J. Org. Chem.* vol. 40, No. 13, Gechwend et al. (1975) pp. 2008–2009.

*Tetrahedron Letters*, No. 51 de Silva et al. (1978) pp. 5107–5110.

*Primary Examiner*—Brian M. Burn
*Attorney, Agent, or Firm*—Charles M. Kinzig; Edward T. Lentz

[57] ABSTRACT

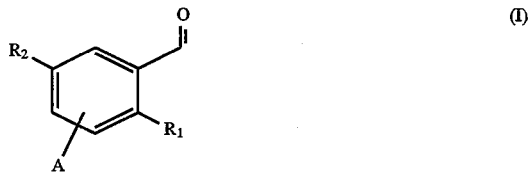

Processes for preparing 2-substituted benzaldehydes of general formula (I), wherein: $R_1$ is $CH_2CH_2$—$(L_1)_p$—$(CH_2)_q$—$(L_2)_r$—$CH_2$—$(T)_2$—Z; $L_1$ and $L_2$ are independently $CH_2CH_2$, CH=CH or C≡C; q is 0 to 8; p, r and s are independently 0 or 1; T is O, S, $CH_2$, CH=CH, C≡C; and Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio, or trifluoromethylthio; and $R_2$ and A are independently H, $CF_3$, $C_{1-4}$alkyl, F, Cl, Br or I; are useful for preparing pharmaceutically active compounds.

21 Claims, No Drawings

PROCESSES AND INTERMEDIATES FOR THE PREPARATION OF 2-SUBSTITUTED BENZALDEHYDES

This application is a 35 USC 371 of PCT/US93/02803, filed Mar. 25, 1993.

FIELD OF THE INVENTION

This invention relates to novel intermediates and processes for preparing useful intermediates in the synthesis of pharmaceutically active agents.

BACKGROUND

2-Substituted benzaldehydes are useful intermediates for preparing pharmaceutically active compounds. For example, certain compounds which are leukotriene antagonists and useful in the treatment of asthma may be prepared from 2-substituted benzaldehydes of the general formula(Ia):

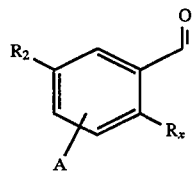

(Ia)

wherein:

$R_x$ is $(L)_a$—$(CH_2)_b$—$(T)_c$—M;

a is 0 or 1;

b is 3 to 14;

c is 0 or 1;

L and T are independently sulfur, oxygen, or $CH_2$; and

M is $C_{1-4}$alkyl, ethynyl, trifluoromethyl, isopropenyl, furanyl, thienyl, cyclohexyl or phenyl optionally mono substituted with Br, Cl, $CF_3$, $C_{1-4}$alkyl, $C_{1-4}$alkoxy, methylthio, or trifluoromethylthio;

$R_2$ and A are independently selected from H, $CF_3$, $C_{1-4}$alkyl, $C_{1-4}$alkoxy, F, Cl, Br, I, OH, $NO_2$ or $NH_2$;

or $R_1$ and A are H and $R_2$ is $(L)_a$—$(CH_2)_b$—$(T)_c$—M wherein a, b, c, L, T, and M are as defined above.

Such compounds are disclosed, for instance in U.S. Pat. No. 4,820,719, U.S. Pat. No. 4,874,792 and EP-A 0 296 732, the disclosures of which are incorporated herein by reference. Accordingly, two general methods for preparing the 2-substituted benzaldehydes are reported therein: 1) palladium catalyzed addition of a substituted 1-alkynyl compound to a 2-halo benzaldehyde effects a coupling to provide a 2-(1-alkynyl)benzaldehyde directly, and 2) a 2-methoxybenzoic acid may be converted to 2-(2-methoxy-phenyl)-4,4-dimethyl-oxazoline and treated with an alkyl or aralkyl Grignard reagent to prepare the corresponding 2-(2-alkyl phenyl)-4,4-dimethyl-oxazoline or 2-(2-aralkyl phenyl)4,4-dimethyl-oxazoline (subsequent treatment of the 2-substituted oxazoline with methyl iodide, reduction with sodium borohydride and subsequent acid hydrolysis produces the corresponding 2-substituted benzaldehyde). The latter method is based upon methods disclosed by Meyers et at., *J. Org. Chem.*, 43, 1372(1978). Similar methods for preparing 2-substituted benzaldehydes are disclosed by Perchonock et al., *J. Med. Chem.*, 28, 1145 (1985). In general, these methods employ reagents which functionally displace substituents upon the aryl ring.

Methods for adding an ortho substituent to an aryl ring by rendering the aryl ring nucleophilic are also known. *Org. Reactions*, 26, 43–61 (1979) discloses that certain functional groups which contain nitrogen heteroatoms and are attached to phenyl rings can stabilize a phenyl ring toward lithiation, preferably in the ortho position. The lithiated site may then be treated with a suitable electrophilic reagent to effect substitution. Functional groups which are reported therein to be particularly effective for this purpose are mono- or di-alkyl amides, amines, N,N-dialkyl hydrazones, imidazolines and oxazolines. De Silva et at., Tetrahedron Lett., 5107 (1978), report an ortho-lithiation of a benzamide using sec-butyllithium and a diisopropyl amine, and Trécourt et al., *J. Org. Chem.*, 53, 1367 (1988), report ortho-lithiation of 2-methoxy-pyridine with methyllithium and a catalytic mount of diisopropylamine. Arylcarbimines, however, are reported to have limited synthetic utility due to their tendency to suffer from reaction at the azomethine linkage and alpha-deprotonation. See *Org. Reactions*, 26, 57–58 (1979). Zeigler et at., *J. Org. Chem.*, 41, 1564 (1976) report that arylcarbimines may be induced to undergo ortho-lithiation if an adjacent ether substituent is present.

In addition, it has been reported that methyl groups can be lithiated if located in the ortho position of benzamides, 2-phenyl imidazolines and 2-phenyl oxazolines. Thus, Watanabe et al., *J. Org. Chem.*, 49, 742 (1984) report chain extension via an ortho-toluamide in the synthesis of isocoumarins; Gschwend, et al., *J. Org. Chem.*, 40, 2008 (1975), report benzylic chain extension via lithiation of 2-(o-tolyl) oxazolines; and Houlihan, U.S. Pat. No. 4,100,165, reports condensation of a dilithiated 2-(o-tolyl)imidazoline with esters and acyl halides.

Current methods for the synthesis of the 2-substituted benzaldehydes of this invention employ expensive reagents or multiple process steps which make them unattractive for commercial preparation of 2-substituted benzaldehydes. There is therefore a need for an efficient alternative method for the preparation of 2-substituted benzaldehydes.

SUMMARY OF THE INVENTION

It is an object of this invention to provide a new and efficient process for the preparation of compounds of formula (Ib):

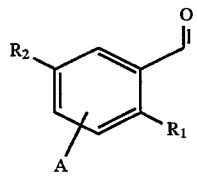

(Ib)

wherein:

$R_1$ is $CH_2CH_2$—$(L_1)_p$—$(CH_2)_q$—$(L_2)_r$—$CH_2$—$(T)_s$—Z;

$L_1$ and $L_2$ are independently $CH_2CH_2$, CH=CH or C≡C;

q is 0 to 8;

p, r and s are independently 0 or 1;

T is O, S, $CH_2$, CH=CH, C≡C; and

Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio, or trifluoromethylthio; and $R_2$ and A are independently H, $CF_3$, $C_{1-4}$alkyl, F, Cl, Br or I.

One feature of this invention is a process for preparing a compound of the formula:

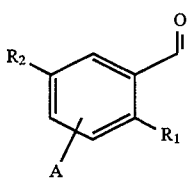

wherein A, $R_1$, $R_2$, $L_1$, $L_2$, q, p, r, s, T and Z are as defined above for formula (Ib), which comprises reacting a compound of the formula:

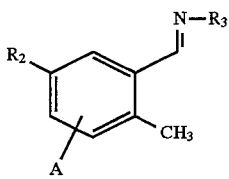

wherein:
$R_2$ and A are as defined above for formula (Ib);
$R_3$ is $C_{1-6}$alkyl, $C_{3-6}$cycloalkyl, $(CH_2)_t$phenyl or $N(R')_2$;
$R'$ is $C_{1-6}$alkyl, $C_{3-6}$cycloalkyl or $(CH_2)_t$phenyl; and
t is 0 or 1;
with a base and a compound of the formula:

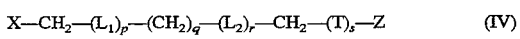

wherein:
$L_1$, $L_2$, p, q, r, s, T and Z are as defined above for formula (Ib), and X is a displaceable group;
and treating the product thereof with acid.

Another feature of this invention is a novel intermediate according to formula (II):

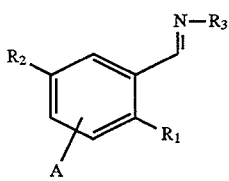

wherein:
$R_1$, $R_2$ and A are as defined for formula (Ib);
$R_3$ is $C_{1-6}$alkyl, $C_{3-6}$cycloalkyl, $(CH_2)_t$phenyl or $N(R')_2$;
$R'$ is $C_{1-6}$alkyl, $C_{3-6}$cycloalkyl or $(CH_2)_t$phenyl; and
t is 0 or 1.

Another feature of this invention is a process for the preparation of the novel intermediate of formula (II), which comprises reacting a compound of the formula (III):

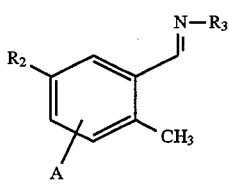

wherein A, $R_2$ and $R_3$ are as defined for formula (II);
with a base and a compound of the formula (IV):

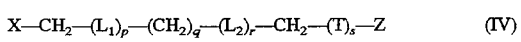

wherein, $L_1$, $L_2$, p, q, r, s, T and Z are as defined above for formula (Ib); and
X is a displaceable group.

Yet another feature of this invention is an improved process for preparing a compound of the formula (II), which comprises adding a catalytic amount of an organic amine to the reaction mixture prior to addition of the base.

Still another feature of this invention is an improved process for preparing a compound of the formula (II), which comprises adding a sodium or potassium alkoxide to the reaction mixture.

Another feature of this invention is an improved process for preparing a compound of the formula (II), which comprises conducting the reaction within a specified temperature range.

DETAILED DESCRIPTION OF THE INVENTION

The present invention discloses useful intermediates and a process for the preparation of compounds of formula (Ib):

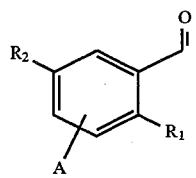

wherein:
$R_1$ is $CH_2CH_2-(L_1)_p-(CH_2)_q-(L_2)_r-CH_2-(T)_s-Z$;
$L_1$ and $L_2$ are independently $CH_2CH_2$, $CH=CH$ or $C\equiv C$;
q is 0 to 8;
p, r and s are independently 0 or 1;
T is O, S, $CH_2$, $CH=CH$, $C\equiv C$; and
Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio, or trifluoromethylthio; and
$R_2$ and A are independently H, $CF_3$, $C_{1-4}$alkyl, F, Cl, Br or I, which comprises reacting a compound of the formula:

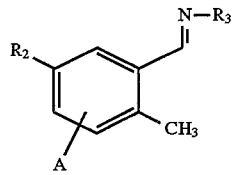

wherein:
$R_2$ and A are as defined above;
$R_3$ is $C_{1-6}$alkyl, $C_{3-6}$cycloalkyl, $(CH_2)_t$phenyl or $N(R')_2$;
$R'$ is $C_{1-6}$alkyl, $C_{3-6}$cycloalkyl or $(CH_2)_t$phenyl; and
t is 0 or 1;
with a base and a compound of the formula:

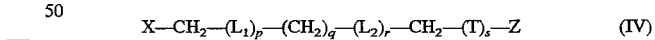

wherein:
$L_1$, $L_2$, p, q, r, s, T and Z are as defined above; and
X is a displaceable group;
and treating the product thereof with acid.

Accordingly, this invention discloses novel intermediates according to formula (II):

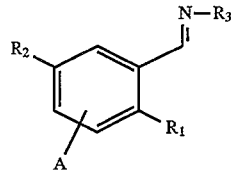

wherein:
$R_1$ is $CH_2CH_2-(L_1)_p-(CH_2)_q-(L_2)_r-CH_2-(T)_s-Z$;

$L_1$ and $L_2$ are independently $CH_2CH_2$, $CH=CH$ or $C\equiv C$;
q is 0 to 8;
p, r and s are independently 0 or 1;
T is O, S, $CH_2$, $CH=CH$, $C\equiv C$; and
Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio, or trifluoromethylthio;

$R_2$ and A are independently H, $CF_3$, $C_{1-4}$alkyl, F, Cl, Br or I;

$R_3$ is $C_{1-6}$alkyl, $C_{3-6}$cycloalkyl, $(CH_2)_t$phenyl or $N(R')_2$;

R' is $C_{1-6}$alkyl, $C_{3-6}$cycloalkyl or $(CH_2)_t$phenyl; and t is 0 or 1.

Suitably Z is phenyl and $L_1$ and $L_2$ are $CH_2CH_2$.
Suitably $R_3$ is t-butyl.
Suitably p, r and s are 1.
Suitably q is 0–2.
Suitably T is $CH_2$ or $C\equiv C$.

A preferred compound is N-[2-(8-phenyloctyl)phenyl]-methylene]-1,1-dimethylethanamine.

The novel intermediates of formula (II) are prepared by a process which comprises reacting a compound of formula (III):

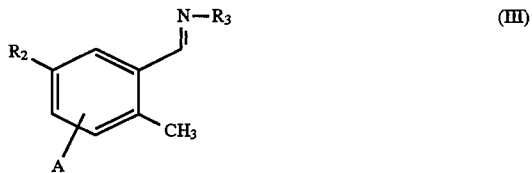

wherein:

$R_2$ and A are independently H, $CF_3$, $C_{1-4}$alkyl, F, Cl, Br or I;

$R_3$ is $C_{1-6}$alkyl, $C_{3-6}$cycloalkyl, $(CH_2)_t$phenyl or $N(R')_2$;

R' is alkyl, cycloalkyl or $(CH_2)_t$phenyl; and t is 0 or 1;

with a base and a compound of the formula (IV):

$$X-CH_2-(L_1)_p-(CH_2)_q-(L_2)_r-CH_2-(T)_s-Z \quad (IV)$$

wherein:

$L_1$ and $L_2$ are independently $CH_2CH_2$, $CH=CH$ or $C\equiv C$;
q is 0 to 8;
p, r and s are independently 0 or 1;
T is O, S, $CH_2$, $CH=CH$ or $C\equiv C$; and
Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio or trifluoromethylthio; and X is a displaceable group.

In a preferred embodiment, this invention discloses a process for preparing a compound of formula (Ib) which comprises reacting a compound of formula (III) with a base and a compound of formula (IV) and treating the reaction mixture with acid. Thus, in the preferred embodiment, the overall conversion is accomplished in a single reaction vessel without isolation of the intermediate product. This process utilizes readily available materials and proceeds in efficient yield in a minimum number of process steps.

Compounds of formula (III) are hydrazones and imines, or Schiff bases, and are generally prepared by any means common to the art for preparing such compounds. One method for preparing the imines comprises reacting a compound of formula (V):

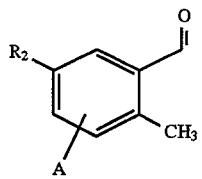

with an amine or a hydrazine of the formula, $R_3$—$NH_2$. Such reactions are normally conducted by admixing the reactants in a non-aqueous solvent and optionally heating the two reactants. Dehydrating agents may be used to drive the reaction towards product if necessary. Common dehydrating agents are, for instance, molecular sieves or magnesium sulfate. Alternatively, dehydration may be effected by azeotroping the water produced by the reaction from an appropriate solvent, such as benzene or toluene. The group $R_3$ is $C_{1-6}$ alkyl, $C_{3-6}$cycloalkyl, benzyl, phenyl or $N(R')_2$. Cyclohexylamine, t-butyl amine, aniline and N,N-dimethyl hydrazine are suitable reagents. t-Butyl amine is preferred.

The electrophile, given by formula (IV), is prepared by conventional methods, such as those disclosed in U.S. Pat. No. 4,820,719, U.S. Pat. No. 4,874,792, EPA 0 296 732 and Perchonock et al., *J. Med. Chem.*, 28, 1145 (1985) which are incorporated herein by reference. The X moiety of the electrophile represents a displaceable group, which may be any group capable of being displaced by the carbon nucleophile prepared from the compound of formula (III). A large number of displaceable groups are suitable, such as alkyl and aryl sulfonates, alkyl and aralkyl acetates, benzoates and halogens. Representative of the class are Cl, Br, I, $R_4SO_3$ and $R_4CO_2$, wherein $R_4$ is $C_{1-4}$alkyl, optionally substituted by 1–5 fluorine atoms, or phenyl, optionally substituted by one or two halogen, $C_{1-4}$alkyl, $C_{1-4}$alkoxy or nitro groups. Representative displaceable groups are toluenesulfonate, bromobenzenesulfonate, nitrobenzene-sulfonate, methanesulfonate, trifluoromethanesulfonate, acetate, chloroacetate, trifluoroacetate, benzoate, bromobenzoate, chlorobenzoate, nitrobenzoate, chloro, bromo and iodo. Chloro and bromo are preferred. Chloro is especially preferred.

In general, the X group of the compounds of formula (IV), if not present in the precursor, is prepared from the corresponding alcohol by reaction with an appropriate acyl halide, anhydride, sulfonyl halide or appropriate halogenating agent. Typical of such reagents are toluenesulfonyl chloride, bromobenzenesulfonyl chloride, nitrobenzenesulfonyl chloride, methanesulfonyl chloride, acetyl chloride, chloroacetyl chloride, trifluoroacetic anhydride, benzoyl chloride, bromobenzoyl chloride, chlorobenzoyl chloride, nitrobenzoyl chloride, oxallyl chloride or bromide, hydrochloric acid, hydrobromic acid, hydroiodic acid, phosphorous tribromide, phosphorous trichloride, phosphorus oxychloride and carbon tetrabromide with triphenyl phosphine. Compounds of the formula HO—$CH_2$—$(L_1)_p$—$(CH_2)_q$—$(L_2)_r$—$CH_2$—$(T)_s$—Z, wherein T is $CH_2$, $L_1$ or $L_2$ are $CH_2CH_2$, and Z is $C_{1-4}$alkyl or phenyl are generally available commercially. Compounds wherein T is O, S or $C\equiv C$, may be prepared by reacting the compound H-T-Z with a compound of the structure X—$CH_2$—$(L_1)_p$—$(CH_2)_q$—$(L_2)_r$—$CH_2$—X, wherein X, $L_1$, $L_2$, T, p, q and r are as defined above, in the presence of an appropriate base. Compounds wherein T is $CH=CH$ may be prepared by semi-hydrogenation of compounds wherein T is $C\equiv C$, such as with Lindlar's catalyst or 5% palladium on barium sulfate and hydrogen. Hydrogenation with a palladium catalyst, such as 5% palladium on carbon, yields the compound wherein T is $CH_2$. When $L_1$ or $L_2$ are $C\equiv C$ or $CH=CH$ the resulting product may be reduced at a subsequent time to yield a product wherein $L_1$ or $L_2$ are $CH=CH$ or $CH_2CH_2$. For example, 1-bromo-7-phenylheptane is prepared from 1,5-dibromopentane and phenylacetylene in the presence of n-butyl lithium, followed by reduction with hydrogen over a palladium catalyst. In an alternate example, 1-bromo or 1-chloro-7-phenylheptane may be prepared via a copper mediated coupling of benzyl magnesium halide with 1,6-dibromohexane or 1-bromo-6-chlorohexane.

Alkylation of the carbimine of formula (III) is initiated by reacting a compound of formula (III) with a strong base to deprotonate the ortho methyl group. Since the metallated intermediate is reactive with water, the activation reaction is suitably carried out in an inert, dry atmosphere, such as nitrogen or argon, although dry air is sufficient.

The activation reaction is carried out in an aprotic solvent. Suitable solvents for this reaction are common aliphatic or aromatic hydrocarbon solvents which are unreactive to strong bases. Representative of such solvents are diethyl ether, tetrahydrofuran, dioxane, dimethoxyethane, toluene, benzene, pentane, hexane and petroleum ethers, and mixtures thereof. Diethyl ether, dioxane and tetrahydrofuran are preferred. Tetrahydrofuran is especially preferred.

A base of sufficient strength to deprotonate the ortho methyl group is required. Any base capable of effecting such deprotonation without causing appreciable side reactions is suitable. Typical of such bases are an alkali metal alkyl, an alkali metal amine (e.g., a salt of an organic or inorganic amine), or an alkali metal aryl. Representative of such bases are n-butyl lithium, sec-butyl lithium, methyl lithium, phenyl lithium, lithium diisopropylamide, lithium tetramethylpiperidide, lithium diethylamide or lithium amide, or the corresponding sodium or potassium salt of any of these species. Alkyl lithium reagents are especially suitable. n-Butyl lithium, lithium tetramethylpiperidide and lithium diisopropylamide are preferred. It is also within the contemplation of this invention that the metal of the base initially used may be exchanged for another metal, for instance another alkali metal, copper, magnesium or zinc. It is often helpful to use a slight molar excess of base, such as 1% to 25%, to ensure complete metallation. About one molar equivalent is normally satisfactory. It will be apparent to one skilled in the art that certain of these bases, such as alkali metal alkyl or aryl, may be incompatible with a halogen substituent in the carbimine, and that other bases, such as lithium diisopropylamide would be more suitable.

The reaction of a compound of formula (III) with the base is carded out by admixing the two reactants. The reaction should be carried out at a temperature sufficient to cause the base to deprotonate the ortho methyl group, yet not so high as to cause adverse side reactions. Thus, the optimum temperature will be dependent upon the base used and the imine reactant. If the base is a lithium dialkyl amide, typically the reaction is carded out between about −20° C. and 60° C.; suitably, the reaction is carded out between about −10° C. and 40° C.

It has been found that surprisingly improved yields are obtained when the reaction is run using an organolithium base at between about 15° C. to about 35° C. Typically, when strong bases are reacted with compounds which possess a moiety which is susceptible to nucleophilic attack, such as a carbimine function, the reactions are conducted at temperatures of about 0° C. and lower. These lower temperatures are believed to prevent undesirable side reactions, such as nucleophilic attack upon the labile carbimine functionality by the base itself or by the anion created by the action of the base. Unexpectedly, with certain bases, such as n-butyllithium optionally with a catalytic amount of diisopropyl amine or dicyclohexylamine, side reactions are minimized and yields are increased by adding the base to the carbimine at about 15° C. to about 35° C. Conducting the reaction between about 20° C. to about 30° C. is especially suitable. Temperatures above 55° C. generally result in an enhancement of undesirable side reactions.

The electrophile, $X-CH_2-(L_1)_p-(CH_2)_q-(L_2)_r-CH_2-(T)_s-Z$, is typically added upon completion of the metallation reaction. Although the electrophile may be added neat, it is conveniently added in a solvent such as that which has been used to form the metallated intermediate. The reaction is then allowed to stir for about 15 min to about 24 h.

If the imine is to be isolated, the reaction solution is diluted with an appropriate solvent, washed with water and concentrated in vacuo to an oil. If a purified product is desired, the product is purified by distillation, or, if appropriate, by crystallization.

Conversion of a compound of formula (II) to a benzaldehyde is accomplished by stirring the imine with any acid of sufficient strength to cause hydrolysis of the $C=N$ bond. Within the context of this invention mineral acids, organic acids and the like are considered to be sufficiently strong acids. For example, methanesulfonic acid, toluenesulfonic acid, trifluoroacetic acid, benzoic acid, acetic acid, hydrofluoric acid, hydrochloric acid, hydrobromic acid, hydroiodic acid, sulfuric acid, nitric acid and phosphoric acid, are all suitable. Mineral acids are preferred. Hydrochloric add is especially preferred.

In the preferred process, the reaction mixture containing the product (II) is hydrolyzed directly by the addition of acid to the reaction mixture. Generally, the reaction mixture is added to a cooled solution of the acid and thereafter allowed to warm to room temperature. The reaction mixture may be monitored for formation of the desired benzaldehyde, such as by analytical chromatography, but typically the reaction is stirred from about 1 h to about 24 h. The product is then isolated by conventional techniques, such as extractive workup.

An improved process for preparing a compound of the formula (II), comprises adding a catalytic amount of an organic amine to the reaction mixture prior to addition of the base, particularly when an alkyl lithium reagent is used as the base. Higher yields are obtained when a catalytic amount of an organic amine is used than when the amine is absent or when a full molar equivalent of the amine is employed. Suitably the organic amine is a secondary amine. Representative amines are diethylamine, diisopropylamine, dicyclohexylamine, piperidine, 2,6-dimethylpiperidine, and 2,2,6,6-tetramethylpiperidine. Diisopropylamine, dicyclohexylamine, and 2,2,6,6-tetramethylpiperidine are especially suitable. The catalytic amount may be from about 0.01 to about 0.3 molar equivalents of organic amine relative to the carbimine. About 0.01 to about 0.15 molar equivalents is suitable. About 0.01 to 0.1 molar equivalents is typical, depending on the amine used. For instance, about 0.01 to about 0.05 equivalents are useful for diisopropylamine and 2,2,6,6-tetramethylpiperidine.

Still another feature of this invention is an improved process for preparing a compound of the formula (II), which comprises preparing a sodium or potassium salt of the carbimine of formula (III) and reacting the product with a compound of the formula (IV). For instance, the 2-methylphenyl carbimine of formula (III) may be treated with a base such as n-butyllithium or lithium diisopropylamide, to form the lithium salt, and further treated with a sodium or potassium base or salt to form the desired salt by a metal exchange reaction. Sodium or potassium alkoxide, or sodium or potassium trifluoroacetate are representative bases/salts. Reaction of the carbimine salt with a compound of formula (IV), such as 7-phenylheptylchloride, effects alkylation at lower temperatures, and with fewer side reactions, than obtained With the comparable lithium salt of the carbimine. Use of the potassium salt is especially suitable.

The examples which follow illustrate how to make and use the compounds and processes which constitute this invention.

EXAMPLES

The nomenclature and abbreviations common to the chemical an are used in the examples. Unless otherwise noted, reagents were obtained from commercial suppliers and were used without further purification. Tetrahydrofuran, if used as a reaction solvent, was dried over 4Å molecular sieves if necessary. All other solvents were obtained from commercial suppliers as Reagent grade and were used without further purification. All non-aqueous reactions were performed under an atmosphere of dry nitrogen. Melting points were taken on a Thomas-Hoover capillary melting point apparatus and are uncorrected. Liquid chromatography was conducted on a Whatman Partisil® 5 ODS 3 RAC II. Gas chromatographic analysis was performed on a DB-1 30 m×0.53 mm capillary column. IR spectra were recorded on a Perkin-Elmer Model 283 infrared spectrophotometer. FT-IR spectra were obtained on a Nicolet 6000 FT infrared spectrometer. Combustion analyses were run on a Perkin-Elmer 240 C elemental analyzer. Unless otherwise indicated all $^1$H-NMR (proton magnetic resonance) spectra were obtained at 400 MHz, using a Bruker Instruments WM 400 spectrometer in deuterochloroform solution. $^{13}$C-NMR spectra were obtained at 100 MHz. Chemical shifts are reported in ppm ($\delta$) downfield from tetramethylsilane. Annotations to $^1$H-NMR are as follows: s, singlet; d, doublet; t, triplet; br, broad; m, multiplet; J, coupling constant in Hertz.

Example 1

Preparation of 1-bromo-7-phenylheptane

To a stirred solution of 1500 mL (0.15 mol) of 0.1M Li$_2$CuCl$_4$ and 1,6-dibromohexane (456.8 g, 1.87 mol, 1.25 eq) in tetrahydrofuran, at −5 to 0° C., was added a solution of benzyl magnesium chloride (750 mL, 2M in tetrahydrofuran, 1.5 mol) over a 90 min period. The reaction mixture was stirred at 0° C. for 90 min, then quenched carefully with 2.0 L of saturated aqueous ammonium chloride. The internal reaction temperature was kept below 20° C. during the quench. The mixture was stirred for 1 h at room temperature and the layers separated. The organic layer was washed with 20% aqueous sodium chloride (4×500 mL). The organic layer was dried (magnesium sulfate), filtered, and concentrated in vacuo at 45°–50° C. to an amber oil. Purification by fractional vacuum distillation through a 12-inch vacuum-jacketed Vigreux column gave the desired product as a colorless oil (198.2 g, 52%). An analytical sample was prepared by redistillation: bp 123°–124° C. (1.5 mm Hg); FT-IR (neat film) 3100–3000, 3000–2800, 2000–1700, 1604, 1496, 748, 699, 644 cm$^{-1}$; $^1$H NMR (CDCl$_3$, 400 MHz) $\delta$ 7.29–7.16 (m, 5 H), 3.40 (t, 2 H), 2.60 (t, 2 H), 1.88–1.81 (m, 2 H), 1.63–1.60 (m, 2 1.32 (m, 6 H); $^{13}$C NMR (CDCl$_3$, 100 MHz) $\delta$ 142.7, 128.4, 128.2, 125.6, 35.9, 34.0, 32.8, 31.4, 29.1, 28.6, 28.1. Anal. Calcd for C$_{13}$H$_{19}$Br: C, 61.19; H, 7.50; Br, 31.31. Found: C, 61.25; H, 7.59; Br, 31.47.

Example 2

Preparation of 7-chloro-1-phenyl heptane a) 1-bromo-6-chlorohexane,

A mixture of 1,6-hexanediol (30 kg, 254 mol), 48% hydrobromic acid (51.0 kg, 302 mol) and toluene was heated to reflux. Water (34.5 kg) was removed under azeotropic conditions. When distillation ceased the mixture was cooled to 20° C. and extracted with a solution of concentrated hydrochloric acid (69.9 kg) and water (60 L). The phases were separated and the organic phase dried by reheating and removing water by azeotropic distillation. The mixture was cooled to 65° C. and dimethylformamide (1.11 kg) was added. Thionyl chloride (31.41 kg, 264 mol) was added over 45 min while maintaining the temperature between 65°–68° C. The mixture was heated to 109° C. over 1.25 h and cooled to 20° C. It was then washed successively with 20% sodium hydroxide solution (100 L) and water (2×150 L, 1×100 L). Toluene (400 L) was removed under vacuum to yield the bromochlorohexane as a toluene solution (85.5 kg, 55% w/w by assay, 93% yield).

b) 7-chloro-1-phenylheptane

A solution of lithium tetrachlorocuprate [THF 33 L, lithium chloride (0.87 kg, 19.3 mol), cupric chloride (1.4 kg, 10.4 mol)] was added to a solution of benzylmagnesium chloride (160 L of 1.86M, 298 mol) in tetrahydrofuran at 15° C., and the mixture stirred for 30 min. Bromochlorohexane in toluene (85.5 kg of solution, 55% w/w by assay, 47.1 kg, 236 mol) was added over 3 h while maintaining the temperature between 15°–20° C. Stirring was continued for a further 1.25 h. 10% Ammonium chloride solution (263 L) was added over 1 h, maintaining the temperature below 30° C. The phases were separated and the organic phase further washed with ammonium chloride solution (170 L) and 20% sodium chloride solution (3×197 L). The organic solution was concentrated under vacuum to leave an oil (56.8 kg, 77% pure by HPLC assay, 88% corrected yield), which was distilled (b.p. 129°–132° C., 2 mbar) to yield the title compound (70%, 99% pure by GC assay).

Example 3

Preparation of N-[(2-methylphenyl)methylene]-1,1-dimethyl-ethanamine

A stirred solution of o-tolualdehyde (25 g, 0.21 mol), and t-butylamine (27.75 g, 0.38 mol) in toluene (250 mL) was refluxed under standard Dean-Stark conditions for 20 h. The solution was evaporated to an oil which was vacuum distilled (bp 70°–73° C., 0.6 mm Hg) to afford 33.9 g (93%) of product: IR (neat) 2980, 1645, 1605, 1460, 1375, 1210, 960, 910 cm$^{-1}$; $^1$H NMR (400 MHz, CDCl$_3$) $\delta$ 8.56 (s, 1 H), 7.86–7.83 (m, 1 H), 7.25–7.11 (m, 3 H), 2.46 (s, 3 H), 1.30 (s, 9 H); $^{13}$C NMR (CDCl$_3$, 100 MHz) $\delta$ 153.7, 137.1, 135.1, 130.5, 129.6, 127.1, 126.4, 57.5, 29.8, 19.2; GC RT 7.6 min (DB-1, 30 m×0.53 mm. program: 100° C. for 5 min, 100°–260° C. at 15° C./min, hold at 260° C. for 12 min).

Example 4

Preparation of 2-methylbenzaldehyde dimethyl hydrazone

A stirred solution of o-tolualdehyde (25.0 g, 0.21 mol), and 1,1-dimethyl hydrazine (25.2 g, 0.42 mol) was refluxed in toluene (200 mL) for 24 h. The solution was concentrated in vacuo and the residual oil was vacuum distilled (51°–60° C., 0.2 mm Hg) to afford the titled product (31.98 g, 94%): IR (neat) 2950, 2850, 1580, 1550, 1455, 1025, 745 cm-1; $^1$H NMR (CDCl$_3$, 400 MHz) δ 7.8–7.6 (m, 1H), 7.4–7.3 (m, 1H), 7.1–6.9 (m, 3H), 2.9 (s, 6H), 2.4 (s, 3H).

Example 5

Preparation of N-[(2-(8-phenyloctyl)phenyl)methylene]-1,1-dimethylethanamine

To a stirred solution of diisopropylamine (29.14 g, 0.289 mol) in tetrahydrofuran (450 mL) cooled to –5° C. was added n-butyllithium (2.5M, 114.3 mL, 0.286 mol) at a rate which maintained the solution temperature below 10° C. After the addition was complete, the solution was stirred 15 min with cooling. To this solution was added N-[(2-methylphenyl)-methylene]-1,1-dimethylethanamine (50.0 g, 0.286 mol) in tetrahydrofuran (65.0 mL) at such a rate as to keep the reaction temperature below 5° C. The reaction was stirred for 15 min with cooling then 1-bromo-7-phenylheptane (72.9 g, 0.286 mol) in tetrahydrofuran (75 mL) was quickly added. The reaction mixture was stirred for 1 h with cooling then allowed to warm to room temperature and stirred for an additional 14 h. The reaction mixture was assayed by gas chromatography for product imine (RT 19.8 min., DB-1, 30 m×0.53 mm, program, 100° C. for 5 min, 100°–260° C. at 15° C./min, hold at 260° C. for 12 min.). The product was isolated by dilution of the reaction mixture with water and methylene chloride, quickly washing the organic mixture with water, and concentrating the solution to an oil. The oil was purified by distillation.

Example 6

Preparation of N-[(2-(8-phenyloctyl)phenyl)-methylene]-1,1-dimethylethanamine

A stirred solution of 2-(8-phenyloctyl)benzaldehyde (10 g, 0.034 mol), and t-butylamine (4.96 g, 0.068 mol) in toluene (100 mL) was refluxed under standard Dean-Stark conditions for 16 h. The solution was evaporated to an oil which was vacuum distilled (bp 260° C., 0.15 mm Hg) to afford the titled product (11.1 g, 94%): GC RT 19.8 min (DB-1, 30 m×0.53 mm, program, 100° C. for 5 min, 100°–260° C. at 15° C./min, hold at 260° C. for 12 min.); $^1$H NMR (CDCl$_3$, 400 MHz) δ 8.58 (s, 1H), 7.86 (d, J=7.5 Hz, 1H), 7.29–7.13 (m, 8H), 2.79 (t, J=7.5 Hz, 2H), 2.58 (t, J=7.5 Hz, 2H), 1.59–1.51 (m, 12H), 1.30 (s, 9H).

Example 7

Preparation of 2-(8-phenyloctyl)benzaldehyde

Via hydrolysis of N-[(2-(8-phenyloctyl)phenyl)methylene]-1,1-dimethylethanamine

To a solution of N-[(2-(8-phenyloctyl)phenyl)methylene]-1,1-dimethylethanamine (0.51 g, 0.0146 mol) in tetrahydrofuran (5 mL) was added 10% aqueous hydrochloric acid (5 mL) and the mixture stirred for 15 h at room temperature. Methylene chloride (10 mL) and water (10 mL) were added and the layers separated. The aqueous layer was extracted with methylene chloride (1×15 mL) and the combined organics were dried (magnesium sulfate), filtered and concentrated in vacuo to an oil (0.405 g, 97.4% pure by HPLC assay, 92% corrected yield): IR (neat) 2920, 2880, 1695, 1600, 1455 cm$^{-1}$; $^1$H NMR (CDCl$_3$, 400 MHz) δ 10.25 (s, 1 H), 7.80 (dd, 1 H, J=1.2 and 7.7 Hz), 7.45 (m, 1 H), 7.33–7.13 (m, 7 H), 2.98 (t, 2 H, J=7.7 Hz), 2.58 (t, 2 H, J=7.7 Hz), 1.58 (m, 4 H), 1.30 (m, 8H).

Example 8

Preparation of 2-(8-phenyloctyl)benzaldehyde

Using one mole equivalent of a nitrogenous base and 1-bromo-7-phenylheptane

To a stirred solution of diisopropylamine (29.14 g, 0.289 mol) in tetrahydrofuran (450 mL) cooled to –5° C. was added n-butyllithium (2.5M, 114.3 mL, 0.286 mol) at a rate which maintained the solution temperature below 10° C. After the addition was complete, the solution was stirred 15 min with cooling. To this solution was added N-[(2-methylphenyl)-methylene]-1,1-dimethylethanamine (50.0 g, 0.286 mol) in tetrahydrofuran (65.0 mL) at such a rate as to keep the reaction temperature below 5° C. The reaction was stirred for 15 min with cooling then 1-bromo-7-phenylheptane (72.9 g, 0.286 mol) in tetrahydrofuran (75 mL) was quickly added. The reaction mixture was stirred for 1 h with cooling then allowed to warm to room temperature and stirred for an additional 14 h. The reaction mixture was quenched with aqueous 10% hydrochloric acid solution, and was stirred for 1 h at 0° C., then at ambient temperature for 14 h. The reaction mixture was poured into methylene chloride (700 mL) and stirred for 5 min. The organic layer was removed, and the aqueous layer extracted with methylene chloride (2×700 mL). The combined organic layers were washed with 10% hydrochloric acid (2×500 mL) and saturated brine (1×350 mL), then concentrated in vacuo to a golden oil. The crude product was passed through a Pope Still (100° C., 0.2 mm Hg) and the residue treated with hexane (400 mL) with stirring for 5 min. The solution was allowed to settle, and decanted. The hexane treatment was repeated an additional two times, and the combined hexane washes were then filtered through a Celite® plug and concentrated to a light yellow oil (72.5 g, 92.4% pure by HPLC assay, 82% corrected yield). For analytical purposes, a small sample was further purified by Kugelrohr distillation (250° C., 0.1 mm Hg): IR (neat) 2910, 1695, 1600, 1450, 1210, 1190 cm$^{-1}$; $^1$H NMR (CDCl$_3$, 400 MHz) δ 10.25 (s, 1 H), 7.80 (dd, 1 H, J=1.2 and 7.7 Hz), 7.45 (m, 1 H), 7.33–7.13 (m, 7 H), 2.98 (t, 2 H, J=7.7 Hz), 2.58 (t, 2 H, J=7.7 Hz), 1.58 (m, 4 H), 1.30 (m, 8 H); $^{13}$C NMR (CDCl$_3$, 100 MHz) δ 192.2, 145.7, 142.8, 133.7, 133.6, 131.3, 130.9, 128.3, 128.2, 126.3, 125.5, 35.9, 32.4, 32.4, 31.4, 29.5, 29.4, 29.3, 29.2; HPLC RT 5.8 min (Whatman Partisil® 5 ODS 3 RAC II, 4.6 mm I.D.×10 cm, 2 mL/min, 7:3 CH$_3$CN:H$_2$O, UV detection at 211 nm).

Example 9

Preparation of 2-(8-phenyloctyl)benzaldehyde

Using two mole equivalents of imine and nitrogenous base and one mole equivalent of 1-chloro-7-phenylheptane A solution of lithium diisopropylamide in THF (15.4 g, 0.024 mol) was added to THF (30 mL) and cooled to –10° C. under a nitrogen atmosphere. A solution of N-[(2-methylphenyl)-methylene]-1,1-dimethylethanamine (4.23 g, 0.024 mol) in THF (5 ml) was added and the mixture was stirred at –10° C. for 20 min. Phenylheptylchloride (2.77 g, 0.012 mol) in THF (5 ml) was added and the mixture was heated to 58° C. GC analysis showed no phenylheptylchloride remaining after 3 h. The mixture was cooled to 0° C. and dilute HCl (50 mL) was added such that the temperature was kept below 25° C. The solution was reheated to 58° C. where it was maintained for 16 h. After cooling to 20° C., methylene chloride (100 ml) was added and the phases were separated. The aqueous phase was further extracted with methylene chloride (50 ml) and the combined organic phases washed with water (100 ml). After drying over magnesium sulphate, filtering and evaporation of the solvent the product was obtained as an oil weighing (6.96 g, 28.6% pure by HPLC assay, 57% corrected yield).

Using the above conditions, but stirring the reaction mixture at ambient temperature for 20 h instead of refluxing for 3 h, a corrected yield of 59% was obtained.

Using the above conditions, but employing one molar equivalent of the carbimine and amine base relative to the phenylheptylchloride, a corrected yield of 42% was obtained.

Example 10

Preparation of 2-(8-phenyloctyl)benzaldehyde

Exchanging potassium for lithium as basic counterion/ using different imines a) N-[(2-methylphenyl)methylene]-1,1-dimethylethanamine (5.00 g, 29 mmol) was added to a solution of lithium diisopropylamide [28.5 mmol; prepared from diisopropylamine (4.0 mL, 2.89 g, 29 mmol) and n-butyl lithium (2.5M, 11.43 mL, 28.5 mmol)] in THF (50 mL) at −10° C. After stirring at this temperature for 75 min, a solution of potassium t-butoxide (1.49M, 19.2 mL, 28.5 mmol) in THF was added. After a further 15 min, 1-chloro-7-phenylheptane (3.77 g, 17.9 mmol) was added. The reaction was allowed to warm to room temperature and stirred for 16 h. Hydrochloric acid (6M, 5 mL) was added and the mixture was refluxed for 90 min. The aqueous layer was separated and extracted with hexane (2×200 mL). The combined organic fractions were dried over sodium sulphate, filtered and the solvents removed by evaporation under reduced pressure to give an oil (7.44 g). Assay of this material showed it to contain 65% w/w phenyloctylbenzaldehyde (4.84 g, 16.5 mmol, 92%).

b) Using the procedure of (a), except substituting N-[(2-methylphenyl)methylene]-isopropylamine and N-[(2-methylphenyl)methylene]-n-butylamine, gave the following results:

| $R_3$ imine substituent | ratio imine:PHC | Yield (%) |
| --- | --- | --- |
| i) t-Bu | 1.6:1 | 92 |
| ii) i-Pr | 2.0:1 | 31 |
| iii) n-Bu | 2.0:1 | ~10 |

Example 11

Preparation of 2-(8-phenyloctyl)benzaldehyde

Use of a catalytic mount of a nitrogen base/comparison of different electrophiles a) phenylheptylbromide/phenylheptyliodide i.) To a solution of N-[(2-methylphenyl)methylene]-1,1-dimethylethanamine (5.0 g, 0.03 mol) and N,N,N',N'-tetramethylethylene diamine (3.31 g, 0.03 mol) in tetrahydrofuran (40 mL), n-butyl lithium (2.5M, 11.4 mL, 0.03 mol) at 0° C. was slowly added. The solution was stirred for an additional 30 min followed by the quick addition of 1-bromo-7-phenylheptane (7.28 g, 0.03 mol) in tetrahydrofuran (10 mL). The reaction mixture was allowed to warm to room temperature and stirring was continued for 15 h. The reaction mixture was quenched with 10% aqueous hydrochloric acid (50 mL) and stirred for 30 min. The layers were separated, methylene chloride (50 mL) was added to the organic layer and the organics were washed with saturated brine solution (50 mL). The organics were then dried (magnesium sulfate), and concentrated to an oil to yield 2-(8-phenyloctyl)benzaldehyde (3.8 g, 45%): IR (neat film) 2920, 2880, 1695, 1600, 1455 cm$^{-1}$; $^1$H NMR (CDCl$_3$, 400 MHz) δ 10.25 (s, 1 H), 7.80 (dd, 1 H, J=1.2 and 7.7 Hz), 7.45 (m, 1 H), 7.33–7.13 (m, 7 H), 2.98 (t, 2 H, J=7.7 Hz), 2.58 (t, 2 H, J=7.7 Hz), 1.58 (m, 4 H), 1.30 (m, 8 H).

ii) Using the procedure of (a)(i), except substituting 1-iodo-7-phenylheptane for 1-bromo-7-phenylheptane, 2-(8-phenyloctyl)benzaldehyde was prepared in 34% yield.

b) 1-bromo-7-phenylheptane/1-chloro-7-phenylheptane i) A solution of N-[(2-methylphenyl)methylene]-1,1-dimethylethanamine (2.8 g, 0.016 mol) and 2,2,6,6-tetramethylpiperidine (0.23 g, 0.0016 mol) in tetrahydrofuran (10 mL) was cooled to −5° C. To this was added n-BuLi (1.6M, 10 mL, 0.016 mol) over 40 min maintaining the temperature at −5° C. A solution of 1-bromo-7-phenylheptane (3.4 g, 0.0133 mol) in tetrahydrofuran (5 mL) was added quickly at −5° C. The temperature quickly rose to 40° C. and after cooling to ambient temperature the mixture was stirred for 1 h. The mixture was quenched by the addition of dilute hydrochloric acid and stirred at ambient temperature for 16 h. The product was isolated in the usual manner (5.0 g, 75% pure, 96% corrected yield).

ii) Using the procedure of (b)(i), except substituting 1-chloro-7-phenylheptane for 1-bromo-7-phenylheptane, phenyloctyl benzaldehyde was prepared in 87% corrected yield.

Example 12

Preparation of 2-(8-phenyloctyl)benzaldehyde

Effect of changing the temperature at which anion is formed for various nitrogen bases.

a) A stirred solution of N-[(2-methylphenyl)methylene]-1,1-dimethylethanamine (11.2 g, 0.064 mol) and 2,2,6,6-tetra-methylpiperidine (0.9 g, 0.0064 mol) in tetrahydrofuran (40 mL) was cooled to −5° C. To this was added n-BuLi (1.6M, 40 mL, 0.064 mol) over 60 min from a syringe pump such that the temperature was maintained below 0° C. The mixture was stirred for 30 min and 1-chloro-7-phenylheptane (11.23 g, 0.053 mol) in tetrahydrofuran (20 mL) quickly added. The reaction mixture was heated at 50°–55° C. for 2 h. The reaction mixture was cooled to 40° C. and quenched by the slow addition of dilute hydrochloric acid (100 mL of acid diluted with 300 mL of water). Hydrolysis was completed by heating the mixture at 50°–60° C. for 2.5 h. The mixture was cooled to ambient temperature and the organic phase separated. The aqueous phase was extracted with hexane (100 mL) and the combined organic extracts washed with water (100 mL). The extracts were dried over magnesium sulphate and after filtering and washing the filter cake with hexane the organic solution was concentrated under vacuum to give 2-(8-phenyloctyl) benzaldehyde as an oil (14.5 g, 69.3% pure by HPLC assay, 87% corrected yield).

b) To a stirred solution of N-[(2-methylphenyl)methylene]-1,1-dimethylethanamine (21.0 g, 0.12 mol) in tetrahydrofuran (75 mL), n-BuLi (1.54M, 78 mL, 0.12 mol) was added over 1 h such that the temperature was maintained between 20°–30° C. with cooling. The mixture was stirred for 30 min and 1-chloro-7-phenylheptane (21.05 g, 0.1 mol) in tetrahydrofuran (40 mL) was added quickly. The mixture was heated at 50° C. for 3 h and quenched by the slow addition of dilute hydrochloric acid. Hydrolysis was completed by heating the mixture at 50°–60° C. for 2.5 h. The mixture was cooled to ambient temperature and the organic phase separated. The aqueous phase was extracted with hexane, and the combined organic extracts were washed with water. The extracts were dried over magnesium sulphate and, after filtering and washing the filter cake with hexane, the organic solution was concentrated under vacuum to give 2-(8-phenyloctyl)benzaldehyde as an oil (34.56 g, 65.3% pure by HPLC assay, 77% corrected yield).

c) Using the same procedure as in (a) or (b), except varying the nitrogen base and the temperature at which the anion was formed, the following results were obtained:

| Amine | Anion temp. (°C.) | solution yield (%) | impurity (% PHE*) | profile (% PHC**) |
|---|---|---|---|---|
| i) (i-Pr)$_2$NH | −5 | 55 | 7.2 | 17.3 |
| ii) (i-Pr)$_2$NH | 25 | 94 | 1.8 | 0 |
| iii) DCA† | −5 | 48 | 8.6 | 14.9 |
| iv) DCA† | 25 | 83 | 1.7 | 0.1 |
| v) TMP†† | −5 | 87 | 0.6 | 0.4 |
| vi) TMP†† | 25 | 89 | 0.7 | 0.7 |
| vii) — | 0 | 45 | ND | ND |
| viii) — | 25 | 77 | ND | ND |

DCA† = dicyclohexylamine
TMP†† = tetramethylpiperidine
PHE* = phenylheptene
PHC** = phenylheptylchloride d) Using the procedure of (a) or (b), except substituting 1-bromo-7-phenylheptane, the following results were obtained

| Amine | Anion temp. (°C.) | solution yield (%) | impurity (% PHE*) | profile (% PHB***) |
|---|---|---|---|---|
| i) (i-Pr)$_2$NH | 0 | 89 | ND | ND |
| ii) TMP ii) SS/1195/119 | 25 | 96 | ND | ND |

PHB*** = phenylheptylbromide

Many variations of these examples will be apparent to one skilled in the art and this invention is not limited to these examples, but includes all variations encompassed by the claims which follow.

What is claimed is:

1. A process for preparing a compound of the formula:

wherein:

$R_1$ is $CH_2CH_2$—$(L_1)_p$—$(CH_2)_q$—$(L_2)_r$—$CH_2$—$(T)_s$—$Z$;
$L_1$ and $L_2$ are independently $CH_2CH_2$, $CH=CH$ or $C≡C$;
q is 0 to 8;
p, r and s are independently 0 or 1;
T is O, S, $CH_2$, $CH=CH$, $C≡C$; and
Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio, or trifluoromethylthio; and
$R_2$ and A are independently H, $CF_3$, $C_{1-4}$alkyl, F, Cl, Br or I; which comprises reacting a compound of the formula:

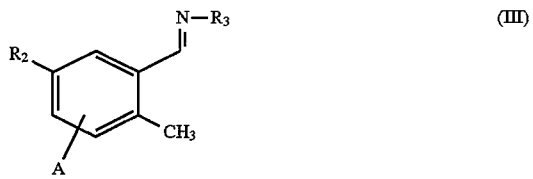

wherein:

$R_2$ and A are as defined above;
$R_3$ is $C_{1-6}$alkyl, $C_{3-6}$cycloalkyl, $(CH_2)_t$phenyl or $N(R')_2$;
R' is $C_{1-6}$alkyl, $C_{3-6}$cycloalkyl or $(CH_2)_t$phenyl; and
t is 0 or 1;
with a lithium alkyl or lithium amine base and a compound of the formula:

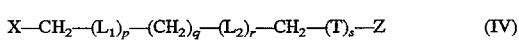

$$X—CH_2—(L_1)_p—(CH_2)_q—(L_2)_r—CH_2—(T)_s—Z \quad (IV)$$

wherein:

$L_1$, $L_2$, p, q, r, s, T and Z are as defined above; and
X is a displaceable group;
and treating the product thereof with acid.

2. A process according to claim 1 in which the base is added to the compound of formula (III) at about 15° C. to about 35° C. and the base is a lithium alkyl or lithium diisopropyl amide.

3. A process according to claim 1 in which $R_2$ and A are H, $R_3$ is t-butyl, and X is bromo or chloro.

4. A process according to claim 1 in which the acid is a mineral acid.

5. A process according to claim 4 in which the acid is hydrochloric acid.

6. A process for preparing 2-(8-Phenyloctyl) benzaldehyde in which N-[(2-methylphenyl)methylene]-1,1-dimethylethanamine is reacted with n-butyllithium and a catalytic amount of an organic amine, and 1-chloro-7-phenylheptane, and subsequently treated with hydrochloric acid.

7. A process for preparing 2-(8-phenyloctyl)benzaldehyde in which N-[(2-methylphenyl)methylene]-1,1-dimethylethanamine is reacted with lithium diisopropyl amide, potassium butoxide, and 1-chloro-7-phenylheptane, and subsequently treated with hydrochloric acid.

8. A process for preparing a compound of the formula:

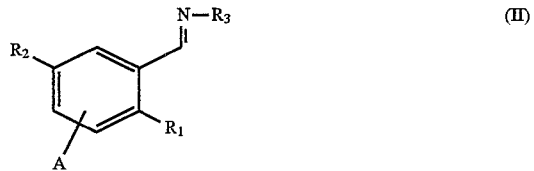

wherein:

$R_1$ is $CH_2CH_2$—$(L_1)_p$—$(CH_2)_q$—$(L_2)_r$—$CH_2$—$(T)_s$—$Z$;
$L_1$ and $L_2$ are independently $CH_2CH_2$, $CH=CH$ or $C≡C$;
q is 0 to 8;
p, r and s are independently 0 or 1;
T is O, S, $CH_2$, $CH=CH$, $C≡C$; and
Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio, or trifluoromethylthio;
$R_2$ and A are independently H, $CF_3$, $C_{1-4}$alkyl, F, Cl, Br or I;
$R_3$ is $C_{1-6}$alkyl, $C_{3-6}$cycloalkyl, $(CH_2)_t$phenyl or $N(R')_2$;

R' is $C_{1-6}$alkyl, $C_{3-6}$cycloalkyl or $(CH_2)_t$phenyl; and
t is 0 or 1;
which comprises reacting a compound of the formula (III):

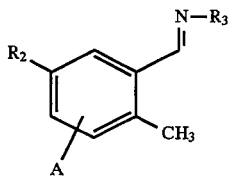

wherein A, $R_2$ and $R_3$ are as defined above;
with a lithium alkyl or lithium amine base and a compound of the formula (IV):

$$X-CH_2-(L_1)_p-(CH_2)_q-(L_2)_r-CH_2-(T)_s-Z \qquad (IV)$$

wherein:
$L_1$, $L_2$, T, Z, p, q, r and s are as defined above; and
X is a displaceable group.

9. A process according to claim 8 in which the base is a lithium alkyl.

10. A process according to claim 8 in which the base is lithium diisopropylamide or butyl lithium.

11. A process according to claim 9 in which a catalytic amount of an organic amine is present.

12. A process according to claim 11 in which the organic amine is diisopropyl amine, 2,2,6,6-tetramethylpiperidine, or dicyclohexylamine, and the organic amine is present in an mount of about 0.01 to 0.15 mole equivalents of the compound of formula (III).

13. A process according to claim 9 in which the base and the compound of formula (III) are reacted at a temperature of about 15° C. to about 35° C.

14. A process according to claim 10 in which a sodium or potassium alkoxide is added to the reaction mixture prior to the addition of the compound of formula (IV).

15. A process according to claim 8 in which $R_3$ is t-butyl.

16. A process according to claim 15 in which X is bromo or chloro.

17. A process according to claim 16 in which Z is phenyl and $L_1$ and $L_2$ are independently $CH_2CH_2$.

18. A compound of the formula:

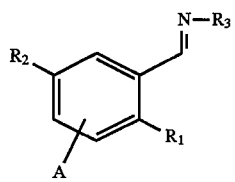

wherein:

$R_1$ is $CH_2CH_2-(L_1)_p-(CH_2)_q-(L_2)_r-CH_2-(T)_s-Z$;

$L_1$ and $L_2$ are independently $CH_2CH_2$, $CH=CH$ or $C\equiv C$;

q is 0 to 8;

p, r and s are independently 0 or 1;

T is O, S, $CH_2$, $CH=CH$, $C\equiv C$; and

Z is $C_{1-4}$alkyl, ethynyl, trifluoromethyl, isopropenyl, furanyl, thienyl, cyclohexyl or phenyl optionally mono substituted with $CF_3$, $C_{1-4}$alkyl, $C_{1-4}$alkoxy, methylthio, or trifluoromethylthio;

$R_2$ and A are independently H, $CF_3$, $C_{1-4}$alkyl, F, Cl, Br or I;

$R_3$ is $C_{1-6}$alkyl, $C_{3-6}$cycloalkyl, $(CH_2)_t$phenyl or $N(R')_2$;

R' is $C_{1-6}$alkyl, $C_{3-6}$cycloalkyl or $(CH_2)_t$phenyl; and
t is 1.

19. A compound according to claim 18 in which $R_3$ is t-butyl.

20. A compound according to claim 18 in Which $L_1$ and $L_2$ are $CH_2CH_2$ and Z is phenyl.

21. A compound according to claim 20 which is N-[(2-(8-phenyloctyl)phenyl)methylene]-1,1-dimethylethanamine.

* * * * *